(12) United States Patent
Schloss

(10) Patent No.: US 6,456,882 B1
(45) Date of Patent: Sep. 24, 2002

(54) IMPLANTABLE CARDIAC STIMULATION DEVICE HAVING AUTOMATIC CAPTURE/THRESHOLD CAPABILITY USING A DYNAMICALLY ADJUSTABLE SAFETY MARGIN

(75) Inventor: Harold C. Schloss, Los Angeles, CA (US)

(73) Assignee: Pacesetter, Inc., Sylmar, CA (US)

(*) Notice: Subject to any disclaimer, the term of this patent is extended or adjusted under 35 U.S.C. 154(b) by 207 days.

(21) Appl. No.: 09/684,153

(22) Filed: Oct. 6, 2000

Related U.S. Application Data
(60) Provisional application No. 60/204,318, filed on May 15, 2000.

(51) Int. Cl.⁷ .................................................. A61N 1/18
(52) U.S. Cl. ................................................. 607/28; 607/9
(58) Field of Search .................................. 607/5, 7, 9, 11, 607/14, 15, 17, 18, 19, 25, 27, 28, 62

(56) References Cited

U.S. PATENT DOCUMENTS

| | | | |
|---|---|---|---|
| 4,712,555 A | 12/1987 | Thornander et al. | 607/17 |
| 4,788,980 A | 12/1988 | Mann et al. | 607/14 |
| 4,809,697 A | 3/1989 | Causey, III et al. | 607/31 |
| 4,940,052 A | 7/1990 | Mann et al. | 607/17 |
| 4,944,298 A | 7/1990 | Sholder | 607/14 |
| 4,944,299 A | 7/1990 | Silvian | 607/32 |
| 6,058,328 A * | 5/2000 | Levine et al. | 607/14 |
| 6,101,416 A * | 8/2000 | Sloman | 607/28 |
| 6,324,427 B1 * | 11/2001 | Florio | 607/28 |
| 6,339,723 B1 * | 1/2002 | Sloman | 607/28 |
| 6,351,672 B1 * | 2/2002 | Park et al. | 607/19 |
| 6,377,851 B1 * | 4/2002 | Shieh et al. | 607/9 |
| 6,377,852 B1 * | 4/2002 | Bornzin et al. | 607/9 |

OTHER PUBLICATIONS

Pacesetter®, "AFFINITY™ DR Model 5330 L/R, Dual–Chamber Pulse Generator with AUTOCAPTURE™ Pacing System", 1998 St. Jude Medical, Inc.

* cited by examiner

*Primary Examiner*—Willis R. Wolfe

(57) ABSTRACT

An improved system and method for performing automatic capture/threshold detection in an implantable cardiac stimulation device or any device capable of stimulating some organ or tissue in the body. In existing systems a threshold stimulation energy level is periodically determined and a working stimulation energy level is then set by increasing the threshold stimulation energy level by a fixed or preprogrammed safety margin, e.g., a fixed voltage level or a percentage safety margin. However, in certain circumstances this safety margin may not be sufficient, resulting in either frequent threshold level determinations or losses-of-capture. To avoid these situations which may be wasteful of battery energy or dangerous for the patient, embodiments of the present invention periodically increase and/or decrease the safety margin according to the performance of the stimulation device, i.e., based upon the frequency of capture.

31 Claims, 5 Drawing Sheets

IMPLANTABLE CARDIAC STIMULATION DEVICE HAVING AUTOMATIC CAPTURE/THRESHOLD CAPABILITY USING A DYNAMICALLY ADJUSTABLE SAFETY MARGIN

This application claims the benefit of U.S. Provisional Application No. 60/204,318, filed May 15, 2000.

FIELD OF THE INVENTION

The present invention is generally directed to an implantable medical device, e.g., a cardiac stimulation device, and is particularly directed to an automatic capture/threshold pacing method for use in such a device.

BACKGROUND OF THE INVENTION

Implantable cardiac stimulation devices are well known in the art. They include implantable pacemakers which provide stimulation pulses to cause a heart, which would normally beat too slowly or at an irregular rate, to beat at a controlled normal rate. They also include defibrillators, which detect when the atria and/or the ventricles of the heart are in fibrillation or a pathologic rapid organized rhythm and apply cardioverting or defibrillating electrical energy to the heart to restore the heart to a normal rhythm. Implantable cardiac stimulation devices may also include the combined functions of a pacemaker and a defibrillator.

As is well known, implantable cardiac stimulation devices sense cardiac activity for monitoring the cardiac condition of the patient in which the device is implanted. By sensing the cardiac activity of the patient, the device is able to provide cardiac stimulation pulses when they are needed and inhibit the delivery of cardiac stimulation pulses at other times. This inhibition accomplishes two primary functions. Firstly, when the heart is intrinsically stimulated, its hemodynamics are generally improved. Secondly, inhibiting the delivery of a cardiac stimulation pulse reduces the battery current drain on that cycle and extends the life of the battery, which powers and is located within the implantable cardiac stimulation device. Extending the battery life will therefore delay the need to explant and replace the cardiac stimulation device due to an expended battery. Generally, the circuitry used in implantable cardiac stimulation devices have been significantly improved since their introduction such that the major limitation of the battery life is primarily the number and amplitude of the pulses being delivered to a patient's heart. Accordingly, it is preferable to minimize the number of pulses delivered by using this inhibition function and to minimize the amplitude of the pulses where this is clinically appropriate.

It is well known that the amplitude of a pulse that will reliably stimulate a patient's heart i.e., its threshold value will change over time after implantation and will vary with the patient's activity level and other physiological factors. To accommodate for these changes, pacemakers may be programmed manually by a medical practitioner to deliver a pulse at an amplitude well above an observed threshold value. To avoid wasting battery energy, the capability was developed to automatically adjust the pulse amplitude to accommodate for these long and short-term physiological changes. In an existing device, the Affinity® DR, Model 5330 L/R Dual-Chamber Pulse Generator, manufactured by the assignee of the present invention an AutoCapture™ pacing system is provided. The User's Manual, ©1998 St. Jude Medical, which describes this capability is incorporated herein by reference. In this system, the threshold amplitude level is automatically determined for a predetermined duration level in a threshold search routine and capture is maintained by a capture verification routine. Once the threshold search routine has determined a pulse amplitude that will reliably stimulate i.e., capture, the patient's heart, the capture verification routine monitors signals from the patient's heart to identify pulses that do not stimulate the patient's heart (indicating a loss-of-capture). Should a loss-of-capture (LOC) occur the capture verification routine will generate a large amplitude (e.g., 4.5 volt) backup pulse shortly after (typically within 80–100 ms.) the original (primary) stimulation pulse. This capture verification occurs on a pulse-by-pulse basis and thus, the patient's heart will not miss a beat. However while capture verification ensures the patient's safety, the delivery of two stimulation pulses (with the second stimulation pulse typically being much larger in amplitude) is potentially wasteful of a limited resource, the battery capacity. To avoid this condition the existing device, monitors for two consecutive loss-of-capture events and only increases the amplitude of the primary stimulation pulse should two consecutive loss-of-capture (LOC) events occur i.e., according to a loss-of-capture criteria. This procedure is repeated, if necessary, until two consecutive pulses are captured, at which time a threshold search routine will occur. The threshold search routine decreases the primary stimulation pulse amplitude until capture is lost on two consecutive pulses and then, in a similar manner to that previously described, increases the pulse amplitude until two consecutive captures are detected. This is defined as the capture threshold. The primary pulse amplitude is then increased by a safety margin value, e.g., 0.3 volts to ensure a primary stimulation pulse whose amplitude will exceed the threshold value and thus reliably capture the patient's heart without the need for frequent backup pulses. In a copending, commonly-assigned application to Paul A. Levine, entitled "An Implantable Cardiac Stimulation Device Having Autocapture/Autothreshold Capability", improved loss-of-capture criteria are disclosed which are based upon X out of the last Y beats, where Y is greater than 2 and X is less than Y. The Levine application is incorporated herein by reference in its entirety.

In some cases automatically determining the stimulation threshold can be energy inefficient. For example, in the case of micro-dislodgment of a stimulation lead, capture may be lost and may be regained at the same primary stimulation pulse energy level, e.g., at the same amplitude. In such a case, the energy dissipated by the pacing pulses and other processing during the threshold search would have been wasted. In other cases, a highly variable threshold would result in frequent losses of capture, frequent threshold searches, and potentially a higher than necessary primary stimulation pulse level (if the higher than normal threshold was transitory) until the next automatic threshold search.

Therefore what is needed is a flexible system that can determine a threshold energy level for the primary stimulation pulse that accommodates threshold variations while limiting the number of automatic threshold searches and thus conserving battery energy.

SUMMARY OF THE INVENTION

The present invention provides an improved system and method for performing automatic capture and threshold detection in an implantable cardiac stimulation device. In existing systems, a threshold stimulation energy level is periodically determined and a working stimulation energy level is then set by increasing the threshold stimulation energy level by a fixed or preprogrammed safety margin, e.g., a fixed voltage level or a percentage safety margin. However, in certain circumstances this safety margin may not be sufficient, resulting in either frequent threshold level determinations or losses-of-capture. To avoid these situations which may be wasteful of battery energy or dangerous for the patient embodiments of the present invention periodically increase and/or decrease the safety margin according to the performance of the stimulation device i.e., based upon the frequency of capture.

A preferred embodiment of an implantable cardiac stimulation device is configured for stimulating a patient's heart through at least one electrode implanted in electrical contact with selected cardiac tissue using a pulse generator configured for electrical coupling to the electrode and configured to generate stimulation pulses at a controlled energy level to thereby stimulate the patient's heart, wherein the controlled energy level is defined by an amplitude component and a duration component. Additionally a detection circuit is configured for electrical coupling to the electrode and configured to receive cardiac signals for determining the presence or absence of an evoked response to each of the stimulation pulses. A preferred device operating under control of a controller, coupled to the pulse generator and the detection circuit, determines the controlled energy level by adding a safety margin value to a threshold controlled energy level at which capture is detected. In embodiments of the present invention, the safety margin value varies according to a safety margin adjustment criteria related to the absence of evoked responses.

In a first aspect of the present invention the safety margin adjustment criteria is specified by the relative number of cardiac cycles that do not have evoked response to those which do have evoked responses. In a first alternative, the number of cardiac cycles without evoked responses can be compared to the total number of cardiac cycles (including cardiac cycles which have intrinsic beats) to determine if the safety margin adjustment criteria has been met. In a next alternative, the number of cardiac cycles without evoked responses can be counted during a specified time period to determine if the safety margin adjustment criteria has been met.

In a next aspect of the present invention, the safety margin value is increased if the safety margin adjustment criteria is met. The increased safety margin value is then incrementally decreased (toward an initial safety margin value) in response to the safety margin adjustment criteria not being met for a specified time period.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense but is made merely for the purpose of describing the general principles of the invention. The scope of the invention should be determined with reference to the claims.

The present invention provides an improved system and method for performing automatic capture and threshold detection in an implantable cardiac stimulation device, e.g., a pacemaker or an implantable cardioverter/defibrillator (ICD).

Figure 1:
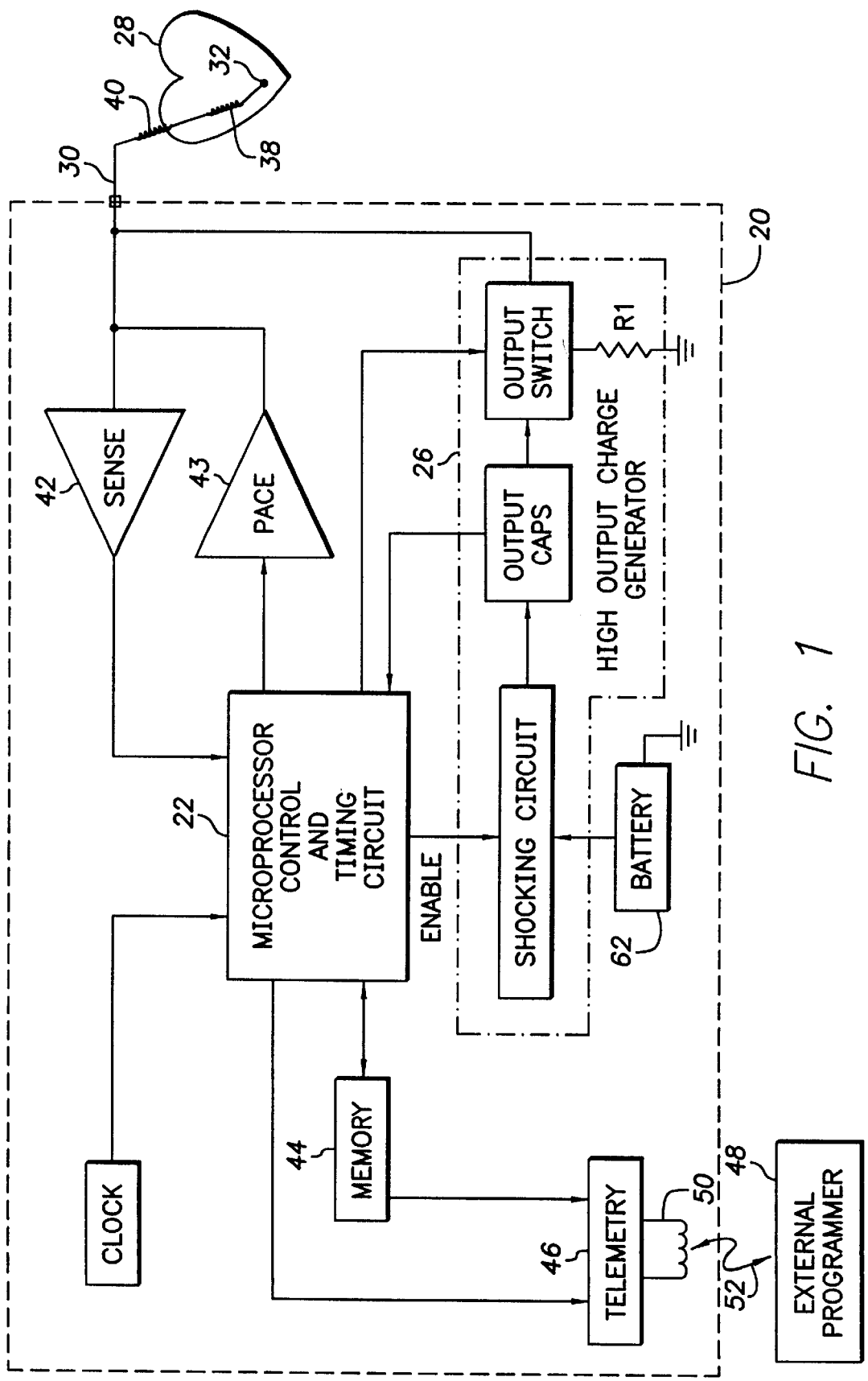
FIG. 1 shows a simplified functional block diagram of an implantable cardioverter/defibrillator (ICD), which represents one type of implantable cardiac stimulation device with which the present invention may be used.
Figure 2:
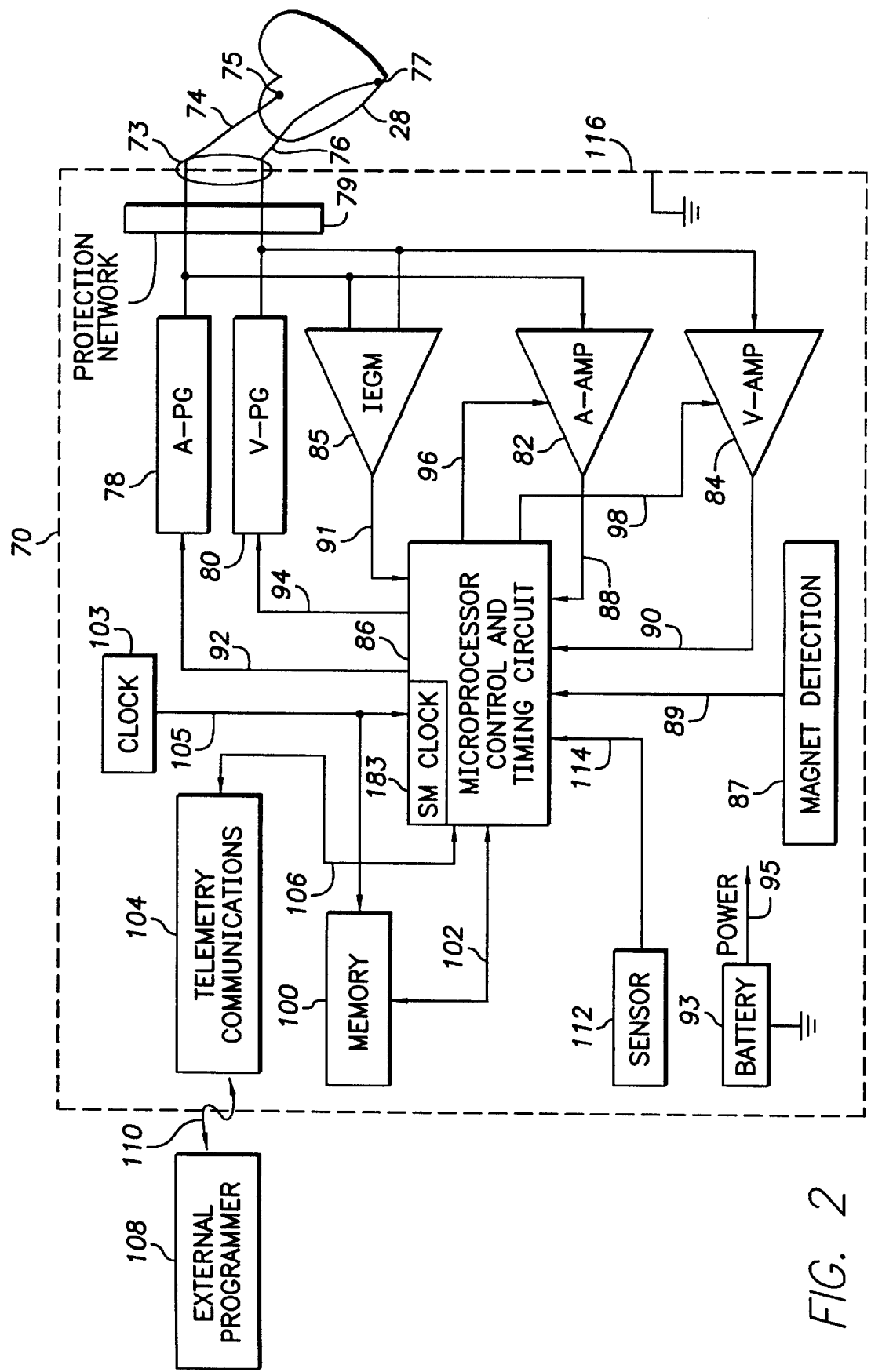
FIG. 2 shows a functional block diagram of an implantable dual-chamber pacemaker, which represents another type of implantable medical device with which the invention may be used.

To better understand the invention, it will first be helpful to have an understanding of the basic functions performed by exemplary implantable stimulation devices with which the invention may be used, e.g., an ICD with dual chamber coils (see FIG. 1) and/or a dual-chamber pacemaker (see FIG. 2). While a dual-chamber device has been chosen for this description this is for teaching purposes only. It is recognized that the present invention could be implemented into a device having one to four chambers, that one of skill in the art could readily adapt the dual-chamber device shown in FIG. 2 to perform single or multiple-chamber functionality, and that a single or multiple chamber device is within the spirit of the invention as is any device capable of delivering stimulating impulses to a tissue or organ of the body.

In FIG. 1 there is shown a simplified functional block diagram of an ICD device 20, and in FIG. 2, there is shown a simplified functional block diagram of a dual-chamber pacemaker 70. It should also be noted that in some instances the functions of an ICD and a pacemaker may be combined within the same cardiac stimulation device. However, for teaching purposes, the devices will be described separately.

It is the primary function of an ICD device to sense the occurrence of a tachyarrhythmia and to automatically apply an appropriate electrical shock therapy to the heart aimed at terminating the tachyarrhythmia. To this end, the ICD device 20, as shown in the functional block diagram of FIG. 1, includes a control and timing circuit (hereinafter referred to as a control/timing circuit) 22, such as a microprocessor, state-machine or other such control circuitry, that controls a high output charge generator 26. The high output charge generator 26 generates electrical stimulation pulses of moderate or high energy (corresponding to cardioversion or defibrillation pulses, respectively), e.g., electrical pulses having energies of from 1 to 10 joules (moderate) or 11 to 40 joules (high), as controlled by the control/timing circuit 22.

Such moderate or high energy pulses are applied to the patient's heart 28 through at least one lead 30 having at least two defibrillation electrodes, such as coil electrodes 38 in the atrium and 40 in the superior vena cava. The lead 30 preferably also includes at least one electrode for pacing and sensing functions, such as electrode 32. Typically, the lead 30 is transvenously inserted into the heart 28 so as to place the coil electrodes 38 and 40 where they are in electrical and preferably physical contact with the patient's heart 28. While only one lead is shown in FIG. 1, it is to be understood that additional defibrillation leads and electrodes may be used to apply the shock treatment generated by the high voltage generator 26 to the patient's heart 28.

The ICD 20 also includes a sense amplifier 42 that is coupled to at least one sensing electrode 32. It is the function of the sense amplifier 42 to sense the electrical activity of the heart 28, as is known in the art, such as R-waves which are the electrical representation of ventricular depolarizations which result in the contraction of ventricular tissue, and P-waves which are the electrical representation of atrial depolarizations which result in the contraction of atrial tissue. Thus, by sensing the ventricular and/or atrial depolarizations through the sense amplifier 42, the control/timing circuit 22 is able to make a determination as to the rate and regularity of the patient's heart beat. Such information, in turn allows the control/timing circuit 22 to determine whether the patient's heart 28 is experiencing an arrhythmia, and to apply appropriate stimulation therapy. Alternatively, a pacing pulse generator 43 can be used to pace the heart in accordance with a preselected pacing strategy. To accomplish this task, the amplitude of pacing pulses generated by the pulse generator 43 is set by the physician to a value above the threshold level for the patient's heart to ensure capture i.e., successful stimulation of the patient's heart. Preferably, the control/timing circuit 22 is configured that in the absence of sensed events detected by the sense amplifier 42, the pacing pulse generator 43 is triggered to deliver pacing pulses at an appropriate rate.

The control/timing circuit 22 further has a memory circuit 44 coupled thereto wherein the operating parameters used by the control/timing circuit 22 are stored. Such operating parameters define, for example, the amplitude of each shocking pulse to be delivered to the patient's heart 28 as well as the duration of these shock pulses. The memory 44 may take many forms, and may be subdivided into as many different memory blocks or sections (addresses) as needed to store desired data and control information. A feature of an exemplary ICD 20 is the ability to sense and store a relatively large amount of data as a data record which data record may then be used to guide the operation of the device i.e., the present operating mode of the device may be dependent, at least in part, on past performance data.

Advantageously the operating parameters of the implantable device 20 may be non-invasively programmed into the memory 44 through a telemetry circuit 46, in telecommunicative contact with an external programmer 48 by way of a suitable coupling coil 50. The coupling coil 50 may serve as an antenna for establishing a radio frequency (RF) communication link 52 with the external programmer 48, or the coil 50 may serve as a means for inductively coupling data between the telemetry circuit 46 and the external programmer 48, as is known in the art. See, e.g., U.S. Pat. Nos. 4,809,697 (Causey, III et al.) and U.S. Pat. No. 4,944,299 (Silvian) incorporated herein by reference. Further, such telemetry circuit 46 advantageously allows status information relating to the operation of the ICD 20, as contained in the control/timing circuit 22 or memory 44, to be sent to the external programmer 48 through the established link 52.

The control/timing circuit 22 includes appropriate processing and logic circuits for analyzing the output of the sense amplifier 42 and determining if such signals indicate the presence of an arrhythmia. Typically the control/timing circuit 22 is based on a microprocessor or similar processing circuit which includes the ability to process or monitor input signals (data) in a prescribed manner, e.g., as controlled by program code stored in a designated area or block of the memory 44. The details of the design and operation of the control/timing circuit 22 are not critical to the present invention. Rather any suitable control/timing circuit 22 may be used that performs the functions described herein. The use design, and operation of microprocessor-based control circuits to perform timing and data analysis functions is known in the art.

The ICD 20 additionally includes a battery 62 which provides operating power to all of the circuits of the ICD 20.

In FIG. 2, a simplified block diagram of the circuitry needed for a dual-chamber pacemaker 70 is illustrated. The pacemaker 70 is coupled to heart 28 by way of leads 74 and 76, the lead 74 having an electrode 75 that is in electrical and preferably physical contact with one of the atria of the heart 28, and the lead 76 having an electrode 77 that is in electrical and preferably physical contact with one of the ventricles of the heart 28. The leads 74 and 76 are electrically and physically connected to the pacemaker 70 through a connector 73 that forms an integral part of the housing wherein the circuits of the pacemaker are housed. Typically, leads 74 and 76 are operated in a bipolar mode where a signal is generated by measuring the voltage difference between the voltage present at a "tip" portion and the "ring" portion on the same lead. Alternatively, leads 74 and 76 can operate in a unipolar mode where the voltage is measured from the "tip" portion of each lead to a conductive case 116 which surrounds the pacemaker 70.

The connector 73 is electrically connected to a protection network 79, which network 79 electrically protects the circuits within the pacemaker 70 from excessive shocks or voltages that could appear on the electrodes 75 and/or 77 in the event such electrodes were to come in contact with a high voltage signal, e.g., from a defibrillation shock.

The leads 74 and 76 carry stimulation pulses to the electrodes 75 and 77 from an atrial pulse generator (A-PG) 78 and a ventricular pulse generator (V-PG) 80, respectively. Further, electrical signals from an atrium are carried from the electrode 75, through the lead 74, to the input terminal of an atrial channel sense amplifier (A-AMP) 82; and electrical signals from a ventricle are carried from the electrode 77 through the lead 76, to the input terminal of a ventricular channel sense amplifier (V-AMP) 84. Similarly, electrical signals from both the atrium and the ventricle are applied to the inputs of an intracardiac electrogram amplifier (IEGM) 85. The amplifier 85 is typically configured to detect an evoked response from the heart 28, i.e., a response to an applied stimulation pulse, thereby aiding in the detection of "capture". Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue. Following each stimulation pulse which causes capture, the associated cardiac tissue (i.e., the atrium or the ventricle) enters into a physiologic refractory period during which it cannot be re-stimulated.

The dual-chamber pacemaker 70 is controlled by a control and timing circuit (hereinafter referred to as a control/timing circuit) 86 that typically includes a microprocessor programmed to carry out control and timing functions. The control/timing circuit 86 receives the sensed signals from the atrial (A-AMP) amplifier 82 over signal line 88. Similarly, the control/timing circuit 86 receives the output signals from the ventricular (V-AMP) amplifier 84 over signal line 90, and the output signals from the IEGM amplifier 85 over signal line 91. These output signals are used to detect intrinsic events, such as R-waves or P-waves. These output signals may also be used to measure the response following a pacing pulse. The control/timing circuit 86 uses these signals to determine if the pacing pulse was captured. Also, the control/timing circuit may be used to measure the polarization artifact present on the electrodes 75 and/or 77 when calibrating the evoked response detection system by pacing when the heart is known to be in a refractory state. The control/timing circuit 86 also generates trigger signals that are sent to the atrial pulse generator (A-PG) 78 and the ventricular pulse generator (V-PG) 80 over signal lines 92 and 94, respectively, to control the energy level (comprised of amplitude and duration components) of the signals delivered to the electrodes, 75 and 77. These trigger signals are generated each time that a stimulation pulse is to be generated by the respective pulse generator 78 or 80. The atrial trigger signal is referred to simply as the "A-trigger", and the ventricular trigger signal is referred to as the "V-trigger".

During the time that either an A-pulse or V-pulse is being delivered to the heart, the corresponding sense amplifier, A-AMP 82 and/or V-AMP 84, is typically disabled by way of a blanking signal presented to these amplifiers from the control/timing circuit 86 over signal lines 96 and 98 respectively. This blanking action prevents the amplifiers 82 and 84 from becoming saturated from the relatively large stimulation pulses that are present at their input terminals during this time. This blanking action also helps prevent residual electrical signals present in the muscle tissue as a result of the pacemaker stimulation from being interpreted as P-waves or R-waves.

As shown in FIG. 2, the pacemaker 70 further includes a memory circuit 100 that is coupled to the control/timing circuit 86 over a suitable data/address bus 102. This memory circuit 100 allows certain control parameters, used by the control/timing circuit 86 in adjusting or programming the operation of the pacemaker 70, to be stored and modified as required, in order to customize the pacemaker's operation to suit the needs of a particular patient. Further, data regarding the operation of the pacemaker 70 (sensed or paced events and activation of any special algorithms or results of interventions) may be stored in the memory 100 for later retrieval and analysis.

As with the memory 44 of the ICD device 20 shown in FIG. 1, the memory 100 of the pacemaker 70 (FIG. 2) may take many forms and may be subdivided into as many different memory blocks or sections (addresses) as needed in order to allow desired data and control information to be stored. A feature of an exemplary cardiac stimulation device is the ability to store a relatively large amount of sensed data as a data record, which data record may then be used to guide the operation of the device. That is, the operating mode of the pacemaker may be dependent, at least in part, on past performance data. For example an average atrial rate may be determined based on the sensed atrial rate over a prescribed period of time. This average rate may then be stored and updated at regular intervals. Such stored rate may then be compared to a present atrial rate and, depending upon the difference, used to control the operating mode of the pacemaker. Other parameters, of course in addition to (or in lieu on atrial rate, may be similarly sensed, stored averaged (or otherwise processed), and then used for comparison purposes against one or more currently-sensed parameters. Advantageously, modern memory devices allow for the storage of large amounts of data in this manner.

A clock circuit 103 directs an appropriate clock signal(s) to the control/timing circuit 86, as well as to any other needed circuits throughout the pacemaker 70 (e.g., to the memory 100) by way of clock bus 105.

A telemetry/communications circuit 104 is further included in the pacemaker 70. This telemetry circuit 104 is connected to the control/timing circuit 86 by way of a suitable command/data bus 106. In turn, the telemetry circuit 104, which is included within the implantable pacemaker 70, may be selectively coupled to an external programmer 108 by means of an appropriate communication link 110. The communication link 110 may be any suitable electromagnetic link such as an RF (radio frequency) channel, a magnetic link an, inductive link, an optical link, and the like. Advantageously, desired commands may be sent to the control/timing circuit 86 through the external programmer 108 and the communication link 110. Similarly, through this communication link 110 with the programmer 108, data commands (either held within the control/timing circuit 86, as in a data latch, or stored within the memory 100) may be remotely received from the programmer 108. Similarly, data initially sensed through the leads 74 or 76, and processed by the microprocessor control circuits 86, or other data measured within or by the pacemaker 70, may be stored and uploaded to the programmer 108. In this manner, non-invasive communications can be established with the implanted pacemaker 70 from a remote, non-implanted, location.

The pacemaker 70 additionally includes a battery 93 which provides operating power to all of the circuits of the pacemaker 70 via a power signal line 95.

It is noted that the pacemaker 70 in FIG. 2 is referred to as a dual-chamber pacemaker because it interfaces with both an atrium and a ventricle of the heart 28. Those portions of the pacemaker 70 that interface with the atrium, e.g., the lead 74, the P-wave sense amplifier 82 the atrial pulse generator 78, and corresponding portions of the control/timing circuit 86, are commonly referred to as the "atrial channel". Similarly, those portions of the pacemaker 70 that interface with the ventricle, e.g., the lead 76, the R-wave sense amplifier 84, the ventricular pulse generator 80 and corresponding portions of the control/timing circuit 86, are commonly referred to as the "ventricular channel". While a dual chamber pacemaker includes a single atrial channel and a single ventricular channel, multichamber devices may include more than one atrial channel and/or more than one ventricular channel.

As needed for certain applications, the pacemaker 70 may further include at least one sensor 112 that is connected to the control/timing circuit 86 of the pacemaker 70 over a suitable connection line 114. While this sensor 112 is illustrated in FIG. 2 as being included within the pacemaker 70, it is to be understood that the sensor may also be external to the pacemaker 70, yet still be implanted within or carried by the patient. A common type of sensor is an activity sensor, such as a piezoelectric crystal, that is mounted to the case of the pacemaker. Other types of sensors are also known, such as sensors that sense the oxygen content of blood, respiration rate, pH of blood body motion, and the like. The type of sensor used is not critical to the present invention. Any sensor or combination of sensors capable of sensing a physiological or physical parameter relatable to the rate at which the heart should be beating (i.e., relatable to the metabolic need of the patient), and/or relatable to whether a tachyarrhythmia is likely to soon occur, can be used. Such sensors are commonly used with "rate-responsive" or "rate-modulated" pacemakers in order to adjust the rate (pacing cycle) of the pacemaker in a manner that tracks the physiological or metabolic needs of the patient.

The pacemaker 70 further includes magnet detection circuitry 87, coupled to the control/timing circuit 86 over signal line 89. It is the purpose of the magnet detection circuitry 87 to detect when a magnet is placed over the pacemaker 70. The magnet may be used by a physician or other medical personnel to perform various reset functions of the pacemaker 70 and/or to signal the control/timing circuit 86 that an external programmer 108 is in place to receive data from, or send data to, the pacemaker memory 100 or control/timing circuit 86 through the telemetry communications circuit 104.

As with the ICD device 20 of FIG. 1, the telemetry or communications circuit 104 may be of conventional design, such as is described in U.S. Pat. No. 4,944,299, or as is otherwise known in the art. Similarly, the external programmer 108 may be of any suitable design known in the art, such as is described in U.S. Pat. No. 4,809,697. Likewise, the memory circuit 100, and the circuits utilized in the atrial and ventricular channels may all be of common design as is known in the pacing art. The present invention is not concerned with the details of the circuitry utilized for each of these pacing elements. Rather, it is concerned with the manner in which the energy level, e.g., amplitude, of the pacing pulses delivered to the heart is determined in coordination with automatic capture and threshold modes of operation. Such determination is controlled by the control/timing circuit 86.

The control/timing circuit 86 may be realized using a variety of different techniques and/or circuits. The preferred type of control/timing circuit 86 is a microprocessor-based control/timing circuit. It is noted, however, that the control/timing circuit 86 could also be realized using a state machine. Indeed, any type of control/timing circuit or system could be employed for the control/timing circuit 86. The present invention is likewise not concerned with the details of the control/timing circuits 22 and 86. Rather, it is concerned with the end result achieved by the control/timing circuit. That is, so long as the control/timing circuit 86 controls the operation of the pacemaker (or other medical device) so that the desired functions are achieved as set forth herein, it matters little what type of control/timing circuit is used. Those of skill in the implantable medical device art, given the teachings presented herein, should thus be able to fashion numerous different types of control/timing circuits that achieve the desired device control.

Representative of the types of control/timing circuits that may be used with the invention is the microprocessor-based control/timing circuit described in U.S. Pat. No. 4,940,052, entitled "Microprocessor Controlled Rate-Responsive Pacemaker Having Automatic Rate Response Threshold Adjustment." Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. The '052, '555, '298 and '980 patents are incorporated herein by reference.

Figure 3:
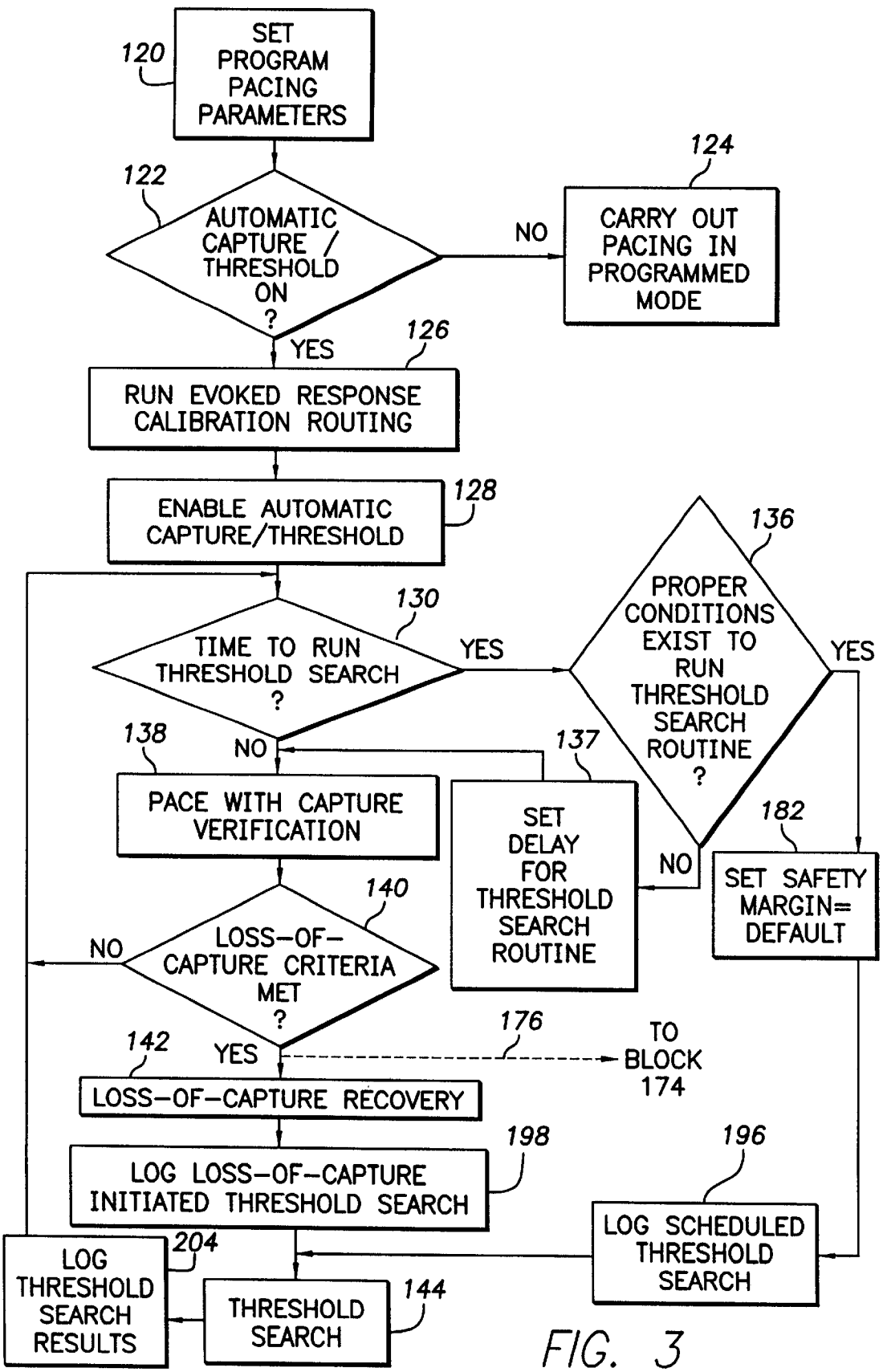
FIG. 3 is a simplified top level flow diagram of the automatic capture/threshold method of the present invention.

FIG. 3 is a simplified top level flow diagram of the automatic capture/threshold method of the present invention. To simplify the discussion this method is described in reference to the dual-chamber pacemaker 70 of FIG. 2. In this case the automatic capture/threshold routines preferably monitor and adjust the amplitude of a ventricular pacing pulse in response to whether an evoked response is sensed. However, one of ordinary skill in the art would recognize the applicability of this method to other such implantable stimulation devices, e.g., the atrial channel of a dual chamber pacemaker, the ICD 20 of FIG. 1, or a muscle stimulation device. Initially all of the pacing parameters required by the pacemaker to operate in a desired program mode are set in block 120 from values in memory 100 or by way of the external programmer 108. In addition to conventional pacing parameters, parameters related to practicing the present invention are preferably preprogrammed and include a definition of: the size of the increase or decrease of the primary stimulation pulse (i.e., the ventricular pacing pulse delivered from the ventricular pulse generator 80) used by the automatic capture/threshold routines; a default amplitude and/or duration for the primary stimulation pulse; how often the periodic automatic threshold search routine is to be invoked (e.g., once a day, every 90 minutes, etc.); and a default working or safety margin. The default safety margin defines how much above the determined capture threshold (i.e., the minimum stimulation energy to cause a ventricular contraction) the ventricular pulse amplitude is to be initially set to provide maintenance of capture during the normal course of events, i.e., the ventricular pulse amplitude is initially set to the determined capture threshold plus a safety margin. In a preferred device these parameters include decreased AV (e.g., 50 ms.) and PV (e.g., 25 ms.) delays to be used during the automatic threshold routine to cause the ventricular stimulation pulse to be issued prior to a potential intrinsic conducted R-wave. This decreased delay allows the heart to respond to stimulation pulses since the stimulation pulses will precede any conducted intrinsic beats after which ventricular tissue would be refractory and additionally, it helps to avoid fusion beats. While these preprogrammed parameters are relevant to the present invention, they are also relevant to the general operation of the pacemaker 70 and thus are set using routine methods, well known to those of skill in the art.

Assuming that all of the pacing parameters were set in block 120, a first determination is made in block 122 as to whether automatic capture/threshold is enabled. If the automatic capture/threshold routine has not been enabled (the NO branch of block 122), the pacemaker 70 resumes cardiac pacing in the desired programmed mode in block 124.

If automatic capture/threshold has been enabled (the YES branch of block 122), the sensitivity of the ventricular 84 amplifier is adjusted in an evoked response calibration routine in block 126 (a similar adjustment can be made of the atrial sense amplifier 82 in the case of automatic capture in the atrium). As is known in the art, the evoked response calibration routine adjusts the evoked response detection sensitivity after measuring the polarization caused by a pacing pulse delivered during the natural refractory period of the heart and the evoked response signal amplitude of a pacing pulse known to capture.

After the automatic capture/threshold routine has been enabled in block 128, a determination is made in block 130 as to whether it is time to initiate a periodic running of the threshold search routine. Typically, the threshold search routine 144 will start automatically at a specified rate which can be preset in the device or a programmable parameter, e.g., once a day every 90 minutes, etc. Also the threshold search routine 144 may be initiated following the completion of the loss-of-capture recovery routine 142.

If it is time to start the threshold search routine 144 (the YES branch of block 130), then a first step is to verify in block 136 that proper conditions exist to accurately perform the threshold search routine (the YES branch of block 136). In general, such conditions require that the pacemaker 70 be engaged in ventricular pacing (generating V-pulses from the ventricular pulse generator 80) at a rate that is below the maximum tracking rate. If the ventricular pulse generator 80 is at the maximum tracking rate, then the proper conditions for executing the threshold search routine 144 do not exist (the NO branch of block 136). As such, the threshold search routine 144 is delayed for a prescribed amount of time in block 137, during which delay the pacemaker 70 continues to operate in its present programmed mode and at its present output level before continuing at block 138. Otherwise the threshold search routine 144 will be processed (following blocks 182 and 196 as discussed below).

If it is not time to commence the threshold search routine 144 (the NO branch of block 130), the pacemaker 70 proceeds to execute the capture verification routine 138 in conjunction with the present pacing mode.

Figure 4A:
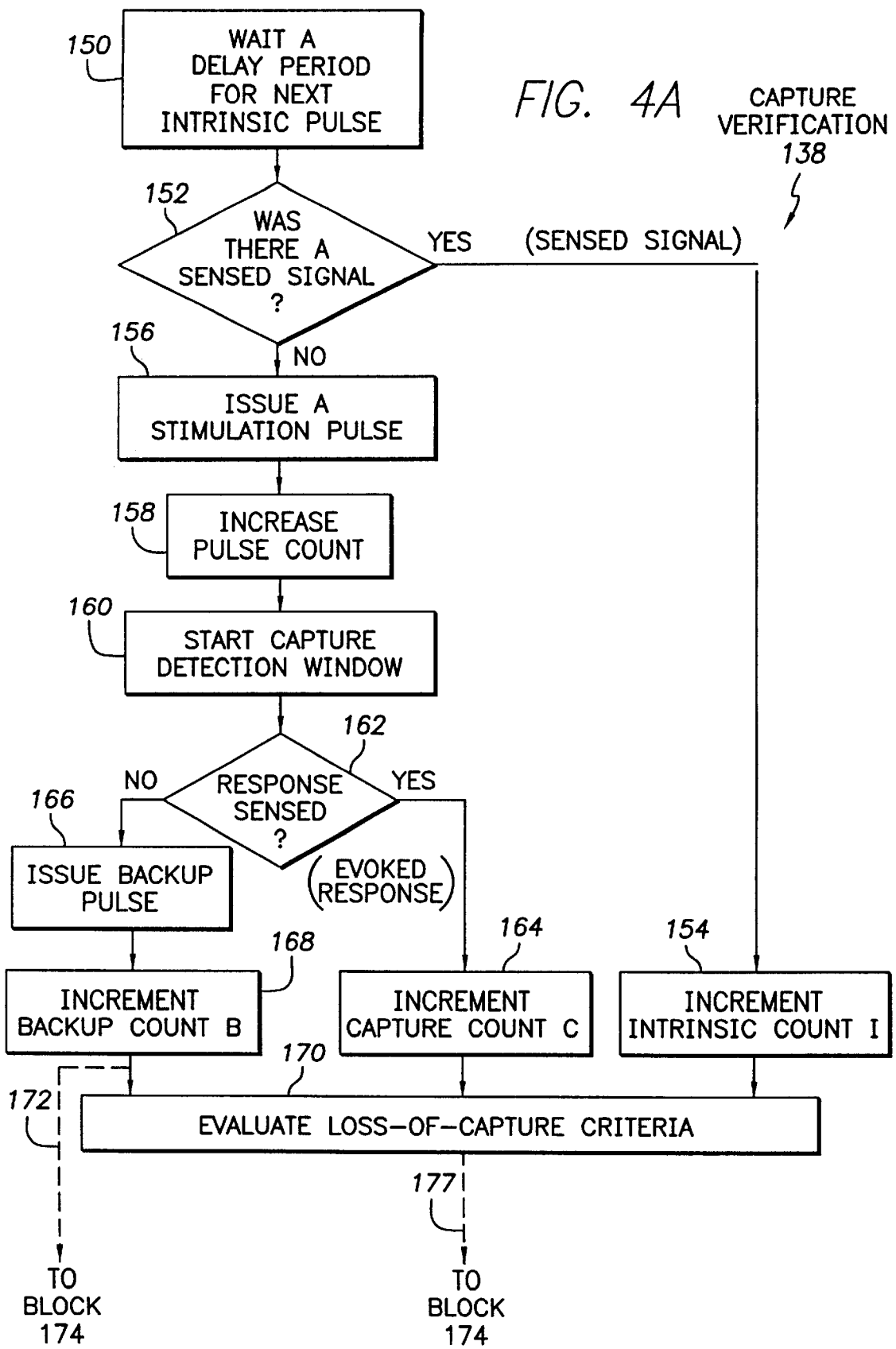
FIGS. 4A and 4B are flow charts of an exemplary capture verification routine as used in FIG. 3 for dynamically adjusting the safety margin in response to the loss-of-capture performance of the implantable device.
Figure 4B:
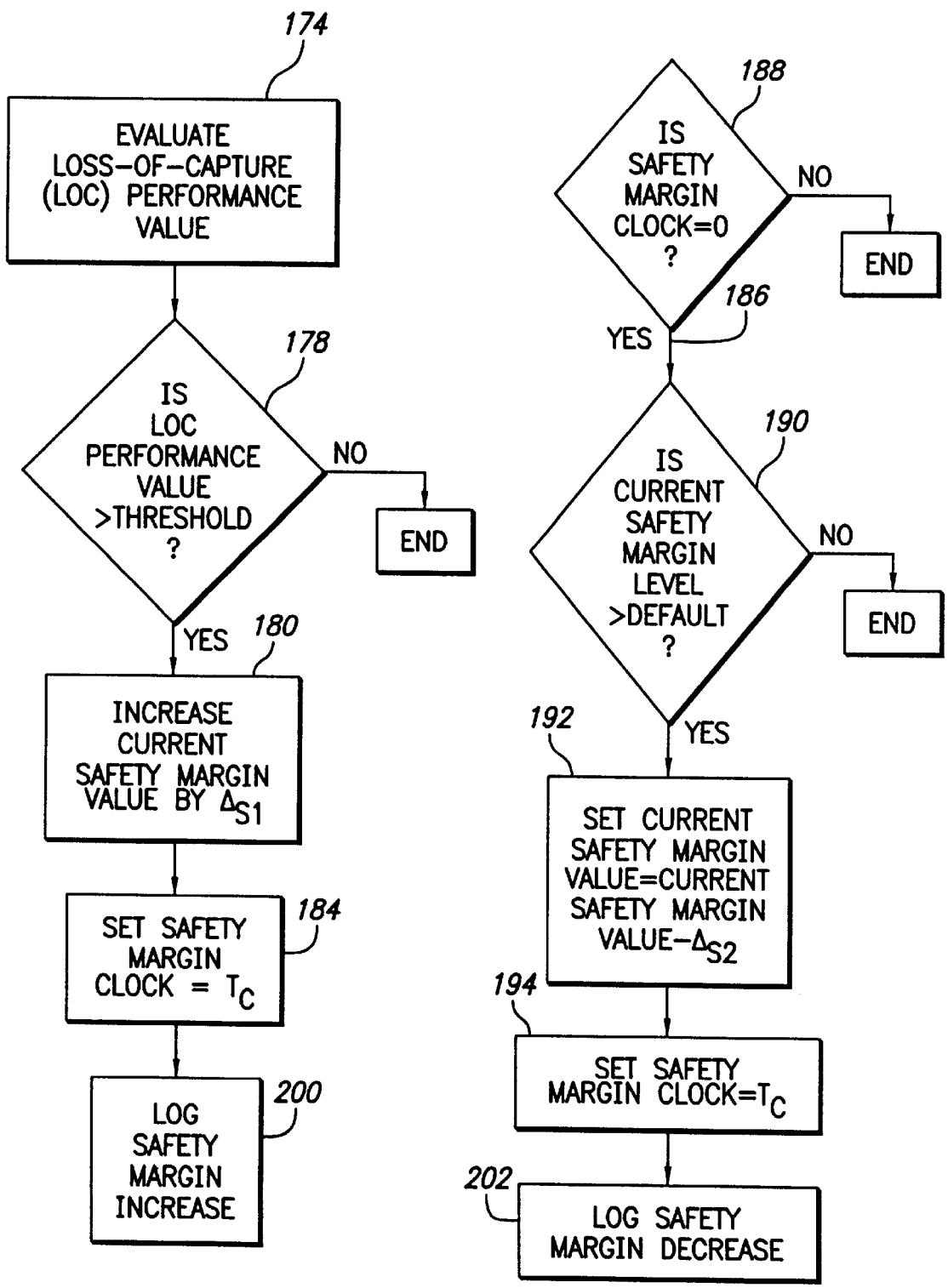

When initiated, the capture verification routine 138 is a continuously running program that performs a loss-of-capture criteria test for each stimulation pulse generated during the programmed pacing sequence. Essentially, the capture verification routine 138 determines for each cardiac cycle whether there was an evoked response corresponding to each stimulation pulse. FIGS. 4A and 4B show a more detailed explanation of an exemplary ventricular capture verification routine 138. Initially, in block 150, the control/timing circuit 86 waits a period of time as determined by the present PV or AV delays. In block 152, the control/timing circuit 86 notes if the ventricular channel sense amplifier 84 has sensed a signal. If a signal was sensed, an intrinsic event (I) is counted in block 154. If a signal was not sensed in block 152 by the end of the PV or AV delay, a ventricular stimulation pulse is issued in block 156 by the ventricular pulse generator 80 at the present stimulation pulse amplitude. Optionally, in block 158 a stimulation pulse count can be incremented. However, since each stimulation pulse will either result in capture (C) or non-capture (i.e., the absence of capture) and a backup pulse. (B), the number of stimulation pulses can be calculated as B+C. In block 160, a capture detection window starts. In an exemplary embodiment, the capture detection window is 60 ms. which is comprised of a 14 ms. absolute refractory period during which time the sense amplifier 84 is blanked from looking for evoked responses, followed by a 46 ms. alert period during which the evoked response is detectable. It is determined in block 162 if, by the end of the capture window, an evoked response was sensed by the ventricular channel sense amplifier 84. If there was an evoked response detected in block 162 during the capture detection window (specifically, anytime during the alert period), a capture count (C) is incremented in block 164. Otherwise, if there was no evoked response detected by the end of the capture detection window, a high amplitude (e.g., 4.5 volt) backup pulse is issued in block 166 and a backup pulse (non-capture) count (B) is increased in block 168. Finally, in block 170, the capture counts are evaluated to determine whether a loss-of-capture criteria has been met. Such criteria may include consecutive losses-of-capture, X losses-of-capture out of the last Y cardiac cycles, etc. If the loss-of-capture criteria is met (block 140 in FIG. 3), a loss-of-capture recovery routine is initiated in block 142 to rapidly increase the stimulation energy level e.g., the pulse amplitude, by increasing the stimulation energy by relatively large (coarse) increments to regain capture at a stimulation energy level that will not require backup pulses. A threshold search routine 144 is then initiated to more precisely (i.e., according to a relatively small (fine) increments) determine the threshold stimulation energy level, e.g., the stimulation pulse amplitude. Once, this threshold stimulation energy level (i.e., the determined capture threshold) is determined, a predetermined safety or working margin value (e.g., an amplitude and/or pulse duration value) is added to the threshold stimulation energy level to determine an initial stimulation energy level. Alternatively, the safety margin value may be a predetermined percentage of the threshold stimulation energy level.

However in embodiments of the present invention the safety margin is variable, adjusting to past performance of the stimulation device. Accordingly, in response to the absence of an evoked response to a stimulation pulse, e.g., see path 172 a loss-of-capture (LOC) performance value, e.g., a percentage is determined in block 174 (see FIG. 4A). Alternatively, this performance value may be evaluated when a loss-of-capture criteria has been met in block 140 (see path 176 in FIG. 3) or in response to each cardiac cycle (see path 177 in FIG. 4A). This performance value may be determined by various methods including comparing: the non-captured cycles (B) to the captured cycles (C), the non-captured cycles (B) to the total paced counts (B+C), the non-captured cycles (B) to the total number of cardiac cycles (B+C+I), etc. Alternatively, a comparison can be made between the number of non-captured cycles (B) and a specified period of time to determine a loss-of-capture rate as a performance value. Subsequently, in block 178, it is determined if the LOC performance value exceeds a specified threshold value i.e., whether a safety margin adjustment criteria has been met. This safety margin adjustment criteria may be preprogrammed or may be programmable from the external programmer 108. For example, a threshold value could be 8 out of the last 100 paced events (i.e., B/(B+C) >0.08) or 8 losses-of-capture in the last 8 minutes. If the LOC performance value exceeds the threshold value (the YES path), the present safety margin value (initially set to a default value) is increased by an increment $\Delta_{s1}$ in block 180. Otherwise, the process completes (the NO path). For example, with an amplitude only safety margin value of 0.3 volts, a $\Delta_{s1}$ value of 0.05 volts could be used and the present safety margin would thus increase to 0.35 volts. Accordingly, in a first variation, the increased safety margin is immediately applied to the present stimulation pulse energy level and thus may avoid the necessity of performing a threshold search. Preferably, the accumulated capture/non-capture data is also reset to enable additional increases in the safety margin if the safety margin adjustment criteria is again met. In a second variation, the increased safety margin value is added to the capture threshold determined the next time that the threshold search 144 occurs (either scheduled or resulting from the loss-of-capture criteria being met).

Preferably, the increased safety margin value (which may represent a transitory physiological condition) is reset (see block 182 in FIG. 3) as part of a periodic invocation of the threshold search routine 144. In another preferred embodiment, the increased safety margin value is decreased back towards its default value if the safety margin adjustment criteria is not met for a specified period of time. Accordingly in an exemplary implementation, a safety margin clock (see SM clock in FIG.2) 183 is set to a terminal count value Tc in block 184. The safety margin clock 183 is then enabled and permitted to count down. When the safety margin clock 183 reaches a value of 0 (e.g., resulting in an interrupt to the control/timing circuit 86) path 186 (the YES path) from block 188 is processed. Otherwise, the process completes (the NO path). It is then determined in block 190 whether the present safety margin value exceeds its default value. If it does not the process completes (the NO path). If the present safety margin does exceed its default value (the YES path), the safety margin value is decreased in block 192, e.g., by $\Delta_{s2}$, toward the default safety margin value. While the decrement value $\Delta_{s2}$ may be the same as the increment value $\Delta_{s1}$, it may also be different. In such a case, block 192 must not allow the safety margin value to decrease below the safety margin default value. If the decrement value $\Delta_{s2}$ would cause the present safety margin value to decrease below its default value, the safety margin value is set to its default value. The safety margin clock 183 is then reset to its terminal count value Tc in block 194 to enable the present safety margin value to decrease again (if necessary) toward its default value at the end of the next time period. Alternatively, if the present safety margin value is already at its default value, step 194 may be skipped and the safety margin clock 182 and associated interrupt may be disabled. Accordingly, the safety margin will dynamically adjust upwards and downwards according to the present loss-of-capture performance of the system.

Preferably, embodiments of the present invention may additionally accumulate statistical data during the aforementioned process. For example, block 196 may log the time of a scheduled threshold search, block 198 may log a threshold search initiated in response to meeting the loss-of-capture criteria, block 200 may log an increase in the safety margin value, block 202 may log a decrease in the safety margin value, and block 204 may log the results of a threshold search. The logged data may be stored in memory 100 as separate events that are preferably time-stamped. Such logged data may be downloaded to the external programmer 108 for display and/or analysis. In another preferred embodiment, the data may be stored in bins in memory 100 that correspond to time periods, safety margin values, threshold values, or any other suitable parameter. This bin data is suitable for display at an external device as a histogram. Thus, at the external programmer 108, the logged data may be displayed either as a historical log or may be formatted (e.g., by the external programmer 108 or the pacemaker 70) for display as a histogram.

Accordingly, what has been shown is an improved automatic capture/threshold procedure for use in an implantable cardiac stimulation device where the safety margin value adaptively varies in response to the loss-of-capture performance of the device. While the invention has been described by means of specific embodiments and applications thereo,f it is understood that numerous modifications and variations could be made thereto by those skilled in the art without departing from the spirit and scope of the invention. For example, while the description of the safety margin has primarily described adding a value to the amplitude of a threshold stimulation pulse, safety margins that increase the duration of the stimulation pulse is also considered to be within the scope of the present invention. Additionally, embodiments where the safety margin is achieved by increasing the amplitude and duration of the stimulation pulse are also considered to be within the scope of the present invention. Such a safety margin has been described in a copending, commonly-assigned U.S. Provisional Application No. 60/204,317, entitled "Method and Device For Optimally Altering Stimulation Energy to Maintain Capture of Cardiac Tissue" (to Mandell), the teachings of which are incorporated herein by reference in their entirety. It is therefore to be understood that within the scope of the claims, the invention may be practiced otherwise than as specifically described herein.

What is claimed is:

1. An implantable cardiac stimulation device for stimulating a patient's heart during a cardiac cycle through at least one electrode implanted in electrical contact with selected cardiac tissue, the stimulation device comprising:
    a pulse generator configured for electrical coupling to the electrode and configured to generate stimulation pulses at a controlled energy level to thereby stimulate the patient's heart, wherein the controlled energy level has an amplitude component and a duration component;
    a detection circuit configured for electrical coupling to the electrode and configured to receive cardiac signals for determining the presence or absence of an evoked response to each of the stimulation pulses;
    a controller coupled to the pulse generator and the detection circuit for determining the controlled energy level by adding a safety margin value to a threshold controlled energy level at which capture is detected; and wherein
    the safety margin value varies according to a safety margin adjustment criteria related to the absence of evoked responses.

2. The cardiac stimulation device of claim 1 wherein the safety margin adjustment criteria is specified by the relative number of cardiac cycles having evoked responses absent to those cardiac cycles having evoked responses present.

3. The cardiac stimulation device of claim 1 wherein the safety margin adjustment criteria is specified by the number of evoked responses absent during a specified time period.

4. The cardiac stimulation device of claim 1 wherein the safety margin adjustment criteria is determined by the number of evoked responses absent during a specified number of cardiac cycles.

5. The cardiac stimulation device of claim 1 wherein the safety margin value includes an amplitude component and a duration component.

6. The cardiac stimulation device of claim 1 wherein the safety margin value is increased in response to satisfying the safety margin adjustment criteria.

7. The cardiac stimulation device of claim 1 wherein the safety margin value is decreased in response to not satisfying the safety margin adjustment criteria for a specified time period.

8. The cardiac stimulation device of claim 1 wherein data is accumulated corresponding to changes in the safety margin value.

9. The cardiac stimulation device of claim 8 wherein the data is accumulated data in bins suitable for display as a histogram by an external device.

10. The cardiac stimulation device of claim 8 wherein the accumulated data is time stamped and is suitable for display by an external device.

11. The cardiac stimulation device of claim 1 wherein the controller determines whether a loss-of-capture criteria has been met in response to absence of evoked response and increases the controlled energy level when a loss-of-capture criteria has been met.

12. The cardiac stimulation device of claim 1 wherein the safety margin adjustment criteria is programmed from an external device.

13. A method for stimulating a patient's heart during a cardiac cycle through at least one electrode implanted in electrical contact with selected cardiac tissue, the method comprising the steps of:
    periodically delivering a stimulation pulse to the selected cardiac tissue, the stimulation pulse having a controlled energy level wherein the controlled energy level is defined by a set of characteristics including an amplitude component and a duration component;
    detecting the presence or absence of an evoked response generated by the selected cardiac tissue in response to the stimulation pulse during a detection window;
    determining whether a safety margin adjustment criteria is satisfied according to the number of cardiac cycles in which an absence of capture has been detected;

adjusting a safety margin value according to the safety margin adjustment criteria;

periodically determining a threshold stimulation energy level at which capture is detected; and determining the controlled energy level by increasing the threshold energy level by the adjusted safety margin value.

14. The method of claim 13 wherein the step of determining whether the safety margin adjustment criteria is satisfied additionally comprises determining the safety margin adjustment criteria according to the relative number of cardiac cycles having evoked response absent to those cardiac cycles having evoked responses present.

15. The method of claim 13 wherein the step of determining whether the safety margin adjustment criteria is satisfied additionally comprises determining the safety margin adjustment criteria according to the number of evoked responses absent during a specified time period.

16. The method of claim 13 wherein the step of determining whether the safety margin adjustment criteria is satisfied additionally comprises determining the safety margin adjustment criteria according to the number of evoked responses absent during a specified number of cardiac cycles.

17. The method of claim 13 wherein the safety margin value includes an amplitude component and a duration component and the step of adjusting the safety margin value comprises the step of adjusting the amplitude and duration components of the safety margin value.

18. The method of claim 13 wherein the adjusting the safety margin value step includes increasing the safety margin value in response to satisfying the safety margin adjustment criteria.

19. The method of claim 13 wherein adjusting the safety margin value step includes decreasing the safety margin value in response to not satisfying the safety margin adjustment criteria for a specified time period.

20. The method of claim 13 additionally comprising the step of accumulating data corresponding to changes in the safety margin value.

21. The method of claim 20 wherein the step of accumulating data includes saving data in bins suitable for display as a histogram by an external device.

22. The method of claim 20 wherein the step of accumulating data includes time stamping the accumulated data in a form suitable for display by an external device.

23. The method of claim 13 additionally comprising the step increasing the controlled energy level when a loss-of-capture criteria has been met.

24. A method for stimulating a patient's heart during a cardiac cycle through at least one electrode implanted in electrical contact with selected cardiac tissue, the method comprising the steps of:

periodically delivering a stimulation pulse to the selected cardiac tissue, the stimulation pulse having a controlled energy level wherein the controlled energy level is defined by a set of characteristics including an amplitude component and a duration component;

detecting the presence or absence of an evoked response generated by the selected cardiac tissue in response to the stimulation pulse during a detection window;

determining whether a safety margin adjustment criteria is satisfied according to the number of cardiac cycles in which an absence of capture has been detected;

adjusting the safety margin value according to the safety margin adjustment criteria; and periodically adjusting the controlled energy level according to the safety margin adjustment criteria.

25. A method for stimulating muscle tissue through at least one electrode implanted in electrical contact with the muscle tissue, the method comprising the steps of:

periodically delivering a stimulation pulse to the muscle tissue, the stimulation pulse having a controlled energy level wherein the controlled energy level is defined by a set of characteristics including an amplitude component and a duration component;

detecting the presence or absence of an evoked response generated by the muscle tissue in response to the stimulation pulse during a detection window;

determining whether a safety margin adjustment criteria is satisfied according to the number of times in which an absence of capture has been detected;

adjusting the safety margin value according to the safety margin adjustment criteria; and periodically adjusting the controlled energy level according to the safety margin adjustment criteria.

26. An implantable cardiac stimulation device for stimulating a patient's heart during a cardiac cycle through at least one electrode implanted in electrical contact with selected cardiac tissue the stimulation device comprising:

means for periodically delivering a stimulation pulse to the patient's heart, the stimulation pulse having a controlled energy level, wherein the controlled energy level is defined by an amplitude component and a duration component;

means for detecting the presence or absence of an evoked response to each of the stimulation pulses;

means for determining a threshold controlled energy level at which capture is detected, means for adding a safety margin value to the determined threshold controlled energy level; and wherein the safety margin value varies according to a safety margin adjustment criteria related to the absence of evoked responses.

27. The cardiac stimulation device of claim 26 wherein the safety margin adjustment criteria is specified by the relative number of cardiac cycles having evoked responses absent to those cardiac cycles having evoked responses present.

28. The cardiac stimulation device of claim 26 wherein the safety margin adjustment criteria is specified by the number of evoked responses absent during a specified time period.

29. The cardiac stimulation device of claim 26 wherein the safety margin adjustment criteria is determined by the number of evoked responses absent during a specified number of cardiac cycles.

30. The cardiac stimulation device of claim 26 wherein the safety margin value includes an amplitude component and a duration component.

31. A system for stimulating a patient's heart during a cardiac cycle, the system comprising:

an electrode implanted in electrical contact with selected cardiac tissue of the patient's heart;

a pulse generator configured for electrical coupling to the electrode and configured to generate stimulation pulses at a controlled energy level to thereby stimulate the patient's heart, wherein the controlled energy level has an amplitude component and a duration component;

a detection circuit configured for electrical coupling to the electrode and configured to receive cardiac signals for determining the presence or absence of an evoked response to each of the stimulation pulses;

a controller coupled to the pulse generator and the detection circuit for determining the controlled energy level by adding a safety margin value to a threshold controlled energy level at which capture is detected; and wherein the safety margin value varies according to a safety margin adjustment criteria related to the absence of evoked responses.

* * * * *